(12) United States Patent
Liu et al.

(10) Patent No.: US 9,121,820 B2
(45) Date of Patent: Sep. 1, 2015

(54) TOP-DOWN FABRICATION METHOD FOR FORMING A NANOWIRE TRANSISTOR DEVICE

(71) Applicant: Taiwan Semiconductor Manufacturing Co., Ltd., Hsin-Chu (TW)

(72) Inventors: Yi-Shao Liu, Zhubei (TW); Fei-Lung Lai, New Taipei (TW); Chun-Wen Cheng, Zhubei (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days.

(21) Appl. No.: 13/974,095

(22) Filed: Aug. 23, 2013

(65) Prior Publication Data
US 2015/0053925 A1  Feb. 26, 2015

(51) Int. Cl.
*H01L 29/66* (2006.01)
*G01N 27/414* (2006.01)
*H01L 29/775* (2006.01)

(52) U.S. Cl.
CPC ...... *G01N 27/4145* (2013.01); *H01L 29/66439* (2013.01); *H01L 29/775* (2013.01)

(58) Field of Classification Search
None
See application file for complete search history.

(56) References Cited

U.S. PATENT DOCUMENTS

| 7,863,071 B1 * | 1/2011 | Ivanov et al. | 438/53 |
| 8,728,844 B1 | 5/2014 | Liu et al. | |
| 2009/0090934 A1 * | 4/2009 | Tezuka et al. | 257/190 |
| 2010/0055699 A1 * | 3/2010 | Kahya | 435/6 |
| 2011/0316565 A1 * | 12/2011 | Guo et al. | 324/679 |
| 2013/0078622 A1 * | 3/2013 | Collins et al. | 435/6.1 |
| 2013/0082242 A1 * | 4/2013 | Han et al. | 257/29 |

OTHER PUBLICATIONS

Chen et al., Silicon nanowire field-effect transistor-based biosensors for biomedical diagnosis and cellular recording investigation, Nano Today (2011) 6, 131-154.*
Hakim et. al., Thin Film Polycrystalline Silicon Nanowire Biosensors, Nano. Lett. 2012, 12, 1868-1872.*
Peidong Yang, et al.; "Semiconductor Nanowires: What's Next?"; Lawrence Berkeley National Laboratory, http://escholarship.org/uc/item/5vn9j2dc; May 9, 2011; p. 1-14.
Alfredo M. Morales, et al.; "A Laser Ablation Method for the Synthesis of Crystalline Semiconductor Nanowires"; Science; vol. 279, Jan. 9, 1998; p. 208-211.
"Of Biomarkers and Biosensors>>Evaluation Engineering"; http://www.evaluationengineering.com/articles/200811/of-biomarkers-and-biosensors.php; Jun. 5, 2013; p. 1-3.
U.S. Appl. No. 13/480,161, filed May 24, 2012.

* cited by examiner

*Primary Examiner* — Charles Garber
*Assistant Examiner* — Alia Sabur
(74) *Attorney, Agent, or Firm* — Eschweiler & Associates, LLC (57) ABSTRACT

The present disclosure relates to a top-down method of forming a nanowire structure extending between source and drain regions of a nanowire transistor device, and an associated apparatus. In some embodiments, the method provides a substrate having a device layer disposed over a first dielectric layer. The device layer has a source region and a drain region separated by a device material. The first dielectric layer has an embedded gate structure abutting the device layer. One or more masking layers are selectively formed over the device layer to define a nanowire structure. The device layer is then selectively etched according to the one or more masking layers to form a nanowire structure at a position between the source region and the drain region. By forming the nanowire structure through a masking and etch process, the nanowire structure is automatically connected to the source and drain regions.

20 Claims, 7 Drawing Sheets

TOP-DOWN FABRICATION METHOD FOR FORMING A NANOWIRE TRANSISTOR DEVICE

BACKGROUND

Traditionally, health care workers wanting to determine the presence of biomarkers within a patient's blood have had to undergo a time consuming process of drawing blood from a patient and performing tests on the drawn blood. Although accurate, current testing methods can be painful to patients that need frequent blood analysis (e.g., diabetic patients) and they do not provide immediate results for patients with rapidly deteriorating conditions.

In recent years, the semiconductor industry has developed biochips configured to detect the presence of certain biomarkers in a patient's blood stream. One common form of biochip uses nanowires serving as the gate of a field effect transistor. Such biochips operate to bring target biomarkers within a medium into contact with a nanowire, thereby producing a change in a current passing through the nanowire. Since current flow of the nanowire varies with the number of charged target molecules, monitoring a change in the IV characteristics of the nanowire provides an accurate indication of the level of the specific functionalized biomarker.

DETAILED DESCRIPTION

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It will be appreciated that the details of the figures are not intended to limit the disclosure, but rather are non-limiting embodiments. For example, it may be evident, however, to one of ordinary skill in the art, that one or more aspects described herein may be practiced with a lesser degree of these specific details. In other instances, known structures and devices are shown in block diagram form to facilitate understanding.

Some nanowire transistor devices (e.g., used in biochips) comprise a nanowire disposed between a source region and a drain region of a field effect transistor. To form such nanowire device, nanowires are typically formed by a bottom-up fabrication process in which a nanowire is grown from particles within a gas. For example, a nanowire may be formed by agitating a silicon and iron target to form a dense hot vapor having silicon and iron species. By condensing the silicon and iron (e.g., as the vapor is cooled through collisions with a buffer gas), the hot vapor condenses into small clusters of silicon and iron to form a nanowire. The nanowire is then connected (i.e., secured) to a source and drain on a semiconductor substrate. While such methods effectively form nanowires, it can be difficult to secure the nanowires to source and drain regions on a semiconductor substrate, thereby making current fabrication methods not suitable for mass production of nanowire transistor devices.

Accordingly, the present disclosure relates to a top-down method of forming a nanowire structure extending between source and drain regions of a nanowire transistor device, and an associated apparatus. In some embodiments, the method comprises providing a substrate having a device layer disposed over a first dielectric layer comprising an embedded gate structure abutting the device layer. The device layer comprises a source region and a drain region separated by a device material (e.g., a semiconductor material). One or more masking layers are selectively formed over the device layer at one or more positions that define a nanowire structure. The device layer is then selectively etched according to the one or more masking layers to form the nanowire structure at a position between the source region and the drain region. By forming the nanowire structure through a masking and etching process, the nanowire structure is automatically connected to the source and drain regions thereby allowing the nanowire transistor device to be mass produced within a fabrication facility.

Figure 1:
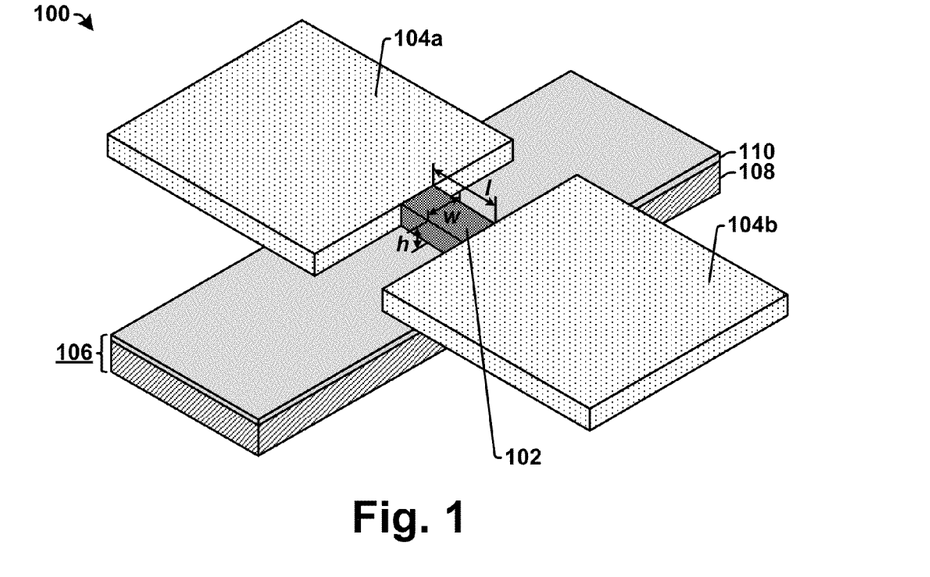
FIG. 1 illustrates some embodiments of a three-dimensional view of a nanowire transistor device having a disclosed nanowire structure.

FIG. 1 illustrates some embodiments of a three-dimensional view of a nanowire transistor device 100 having a disclosed nanowire structure 102.

The disclosed nanowire transistor device 100 comprises a gate structure 106 comprising a gate material layer 108 and a gate dielectric layer 110. In some embodiments, the gate material layer 108 may comprise polysilicon or a gate metal (e.g., aluminum). In some embodiments, the gate dielectric layer 110 may comprise a silicon dioxide, for example.

The disclosed nanowire transistor device 100 further comprises a nanowire structure 102. The nanowire structure 102 is vertically disposed over the gate structure 106 and is separated from the gate material layer 108 by the gate dielectric layer 110. The nanowire structure 102 is laterally disposed between a source region 104a and a drain region 104b. In some embodiments, the nanowire structure 102, the source region 104a, and the drain region 104b may comprise a semiconductor material (e.g., silicon, silicon-germanium, germanium, a III-V semiconductor material, etc.).

The nanowire structure 102 has a height h, a length l, and a width w. The length l of the nanowire structure 102 is greater than the width w or the height h, thereby causing the nanowire structure 102 to have a wire-like structure that connects the source region 104a to the drain region 104b. In various embodiments, the nanowire structure 102 may have a height h, a length l, and a width w with dimensions ranging from tens of nanometers to tens of microns.

In some embodiments, the nanowire transistor device 100 may be comprised within a biosensor (e.g., as described in Kalnitsky et al., U.S. patent application Ser. No. 13/480,161 filed May 24, 2012 entitled "CMOS COMPATIBLE BIOFET", which is hereby incorporated by reference in its entirety) configured to detect the presence of biomarkers, or byproducts from biological reactions, within a medium contacting the nanowire structure 102. For example, as target biomarkers within a medium are brought into contact with the nanowire structure 102, electrical characteristics of the nanowire structure 102 change. Therefore, by monitoring changes in current and/or voltage across the nanowire structure 102, an accurate indication of the level of the biomarker can be detected.

In some embodiments, the height h and width w of the nanowire structure 102 may have dimensions that are comparable to a biomarker, or byproducts from biological reactions, that is to be detected. Since the size of the biomarkers are comparable to a height h and width w of the nanowire structure 102, the presence one or two biomarkers on a surface of the nanowire structure 102 will have a significant impact on a current flowing through the nanowire structure 102, thereby increasing the sensitivity of the nanowire structure as a biosensor. Furthermore, the dimensions of the nanowire structure 102 allow for the nanowire structure 102 to have a relatively small footprint, since sidewalls of the nanowire structure 102 are able to be used as sensing areas for biomarkers.

For example, in some embodiments, the nanowire structure 102 may have a height h and width w that is equal to a range of between approximately 10 nm and approximately 20 nm. Such a height h and width w of the nanowire structure 102 is comparable to a size of a DNA molecule/target comprising a plurality of nucleotides, an RNA molecule/target comprising a plurality of nucleotides, or a protein, thereby increasing the sensitivity of the nanowire structure 102 comprised within a biosensor configured to detect DNA, RNA or a protein (since the presence one or two biomarkers on a surface of the nanowire structure 102 will have a significant impact on a current flowing through the nanowire structure 102). In other embodiments, wherein the nanowire structure 102 is comprised within a biosensor configured to detect bacteria within a medium, the nanowire structure 102 can have a height h and width w that are on the order of microns.

By providing for increased sensitivity in a biosensor, the disclosed nanowire transistor device 100 can lead to improved health care. For example, the increased sensitivity can allow for early detection of cancer through an improved detection of tumor cells within blood. Typically, during the early stages of a tumor, tumor cells may have an extremely low concentration that is 8-9 orders of magnitude lower than that of other blood cells (e.g., for every $10^8$-$10^9$ red blood cells present in a sample, there may be 10 tumor cells). Therefore, for early detection of a tumor, a high level of sensitivity may be needed to detect tumor cells within a blood sample.

Figure 2A:
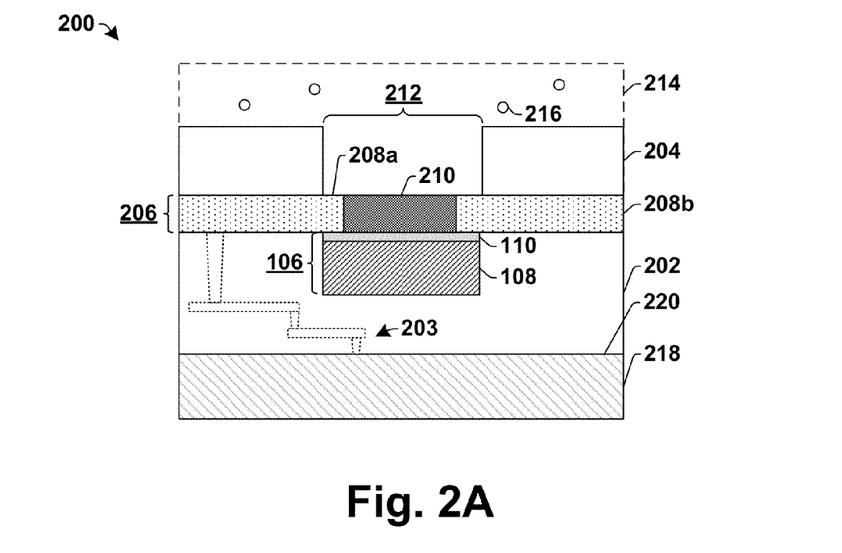
FIGS. 2A-2B illustrate some embodiments of a nanowire transistor device comprising a disclosed nanowire structure.
Figure 2B:
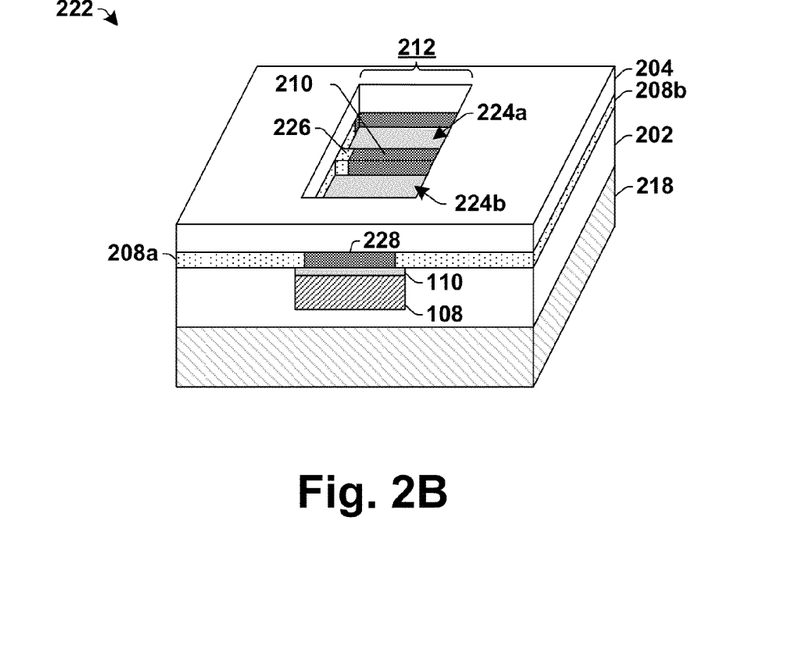

FIGS. 2A-2B illustrate some embodiments of a nanowire transistor device comprising a disclosed nanowire structure 210.

FIG. 2A illustrates some embodiments of a cross-sectional view 200 of a disclosed nanowire transistor device.

The disclosed nanowire transistor device comprises a device layer 206 disposed between an upper, first dielectric layer 202 and a lower, second dielectric layer 204. In some embodiments, the device layer 206 comprises a semiconductor material (e.g., silicon, germanium, etc.) having a source region 208a and a drain region 208b. The source and drain regions, 208a and 208b, are separated by a nanowire structure 210. In some embodiments, the source and drain regions, 208a and 208b, comprise a semiconductor material having a higher concentration of a dopant concentration than the nanowire structure 210.

The first and second dielectric layers, 202 and 204, may comprise an oxide (e.g., $SiO_2$). The first dielectric layer 202 comprises an embedded gate structure 106 having a gate material layer 108 and a gate dielectric layer 110, which separates the gate material layer 108 from the device layer 206. In some embodiments, the gate material layer 108 may comprise a polysilicon layer or a metal gate material (e.g., aluminum). In some embodiments, the gate dielectric layer 110 may comprise an oxide (e.g., $SiO_2$).

In some embodiments, one or more metal interconnect layers 203 are disposed within the first dielectric layer 202. The one or more metal interconnect layers 203 may comprise metal wires configured to provide for lateral connections and metal vias configured to provide for vertical connections. The one or more metal interconnect layers 203 are configured to provide an electrical connection between the source region 208a, the drain region 208b, and/or the gate material layer 108 and an input/output terminal of an integrated chip (e.g., to a bonding pad).

The second dielectric layer 204 is disposed over the device layer 206 along a side of the device layer 206 opposing the gate structure 106. The second dielectric layer 204 comprises an opening 212 that exposes a portion of the device layer 206. For example, the opening 212 may expose a portion of the device layer 206 to a medium 214 (e.g., blood) comprising one or more biomarkers 216, or byproducts from biological reactions. In some embodiments, the second dielectric layer 204 may be disposed onto the device layer 206 and may comprise an opening 212 that exposes the nanowire structure 210 extending between the source region 208a and the drain region 208b to the medium 214. Because the opening 212 is on an opposite side of the nanowire structure 210 as the one or more metal interconnect layers 203, the one or more metal layers 203 can be designed without being restricted by the position of the opening 212.

In some additional embodiments, the opening 212 may expose a portion of the source and/or drain regions, 208a and/or 208b, to the medium 214. By exposing the source and drain regions, 208a and/or 208b, to the medium 214, the target molecules of the medium 214 are able to influence the conductance of the nanowire transistor device (e.g., the resistance of the nanowire structure 210), while the gate material layer 108 acts as a back gate that can control channel electron distribution without a bulk substrate effect. For example, charges within the medium 214 (e.g., from a biomolecule or an electrode within the medium 214) may effect a gate voltage used to turn on the nanowire transistor device.

In some embodiments, the first dielectric layer 202 is coupled to a handle wafer 218 at an interface 220. The position of the interface 220 causes the gate structure 106 to be located between the device layer 206 and the handle wafer 218. The handle wafer 218 comprises a rigid structure that provides structural support to the first and second dielectric layers, 202 and 204. In some embodiments, the handle wafer 218 may comprise a silicon wafer (e.g., having a thickness greater than 200 um).

FIG. 2B illustrates some embodiments of a three-dimensional view 222 of a disclosed nanowire transistor device.

The three-dimensional view 222 illustrates the second dielectric layer 204 disposed over the device layer 206. In some embodiments, the second dielectric layer 204 may be in contact with the source region 208a, the drain region 208b, and a portion of device material 228 (e.g., semiconductor material) that is not comprised within the nanowire structure 210. The opening 212 within the second dielectric layer 204 exposes a portion of the device layer 206 comprising the nanowire structure 210 extending between the source and drain regions, 208a and 208b. The opening 212 allows for the medium 214 to interact with the nanowire structure 210. The device layer 206 comprises a first opening 224a and a second opening 224b, which expose the underlying gate dielectric layer 110 at positions between the source region 208a and the drain region 208b.

In some embodiments, opening 212 may further expose a portion of the source region 208a and/or the drain region 208b. The opening 212 thereby further allows for target molecules in the medium 214 to interact with the source region 208a and/or the drain region 208b, as described above. In some embodiments the source and drain regions, 208a and 208b, may comprise a substantially flat sidewall that extends into the opening 212 so as to expose a portion of the source and drain regions, 208a and 208b, to the opening 212. In other embodiments, the source and/or drain regions, 208a and/or 208b, may comprise a bulge 226 of doped semiconductor material (i.e., the source and drain regions are not square, but instead comprise a square shape having a bulge) that protrudes from sidewalls of the source and/or drain regions, 208a and/or 208b, to a position that is within the opening 212. The bulge 226 is configured to connect the source and/or drain regions, 208a and/or 208b, underlying the second dielectric layer 204 to the nanowire structure 210, in a manner that minimizes the leakage by minimizing the exposure of the source and drain regions, 208a and 208b.

Figure 3:
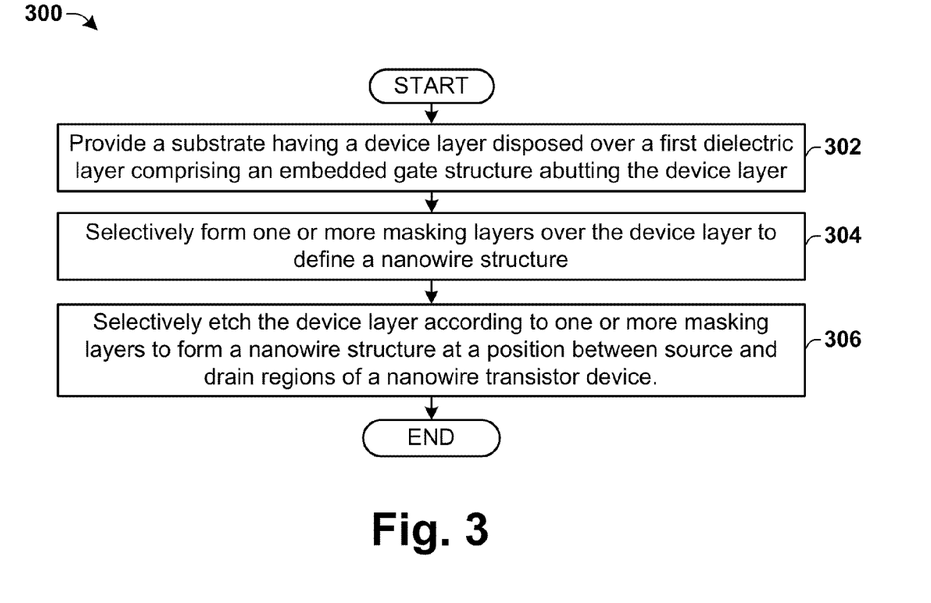
FIG. 3 illustrates some embodiments of a top-down method of forming a disclosed nanowire structure on a nanowire transistor device.

FIG. 3 illustrates some embodiments of a top-down method 300 of forming a disclosed nanowire structure on a nanowire transistor device. As described in more detail below, the method 300 first forms a substrate having a device material (e.g., a semiconductor material) and then selectively etches the device material to form a nanowire structure.

At 302, a substrate having a device layer disposed over a first dielectric layer is provided. The device layer comprises a source region and a drain region separated by a device material (e.g., a semiconductor material). The first dielectric layer comprises an embedded gate structure, having a gate material layer and a gate dielectric layer, abutting the device layer.

At 304, one or more masking layers are selectively formed over the device layer at positions that define a nanowire structure. The one or more masking layers may be selectively formed over the device layer using a photolithography process. For example, a photoresist material may be deposited onto the device layer and then selectively exposed and developed to form one or more masking layers.

At 306, the device layer is selectively etched according to the one or more masking layers to form a nanowire structure at a position between the source region and the drain region of a nanowire transistor device.

Figure 4:
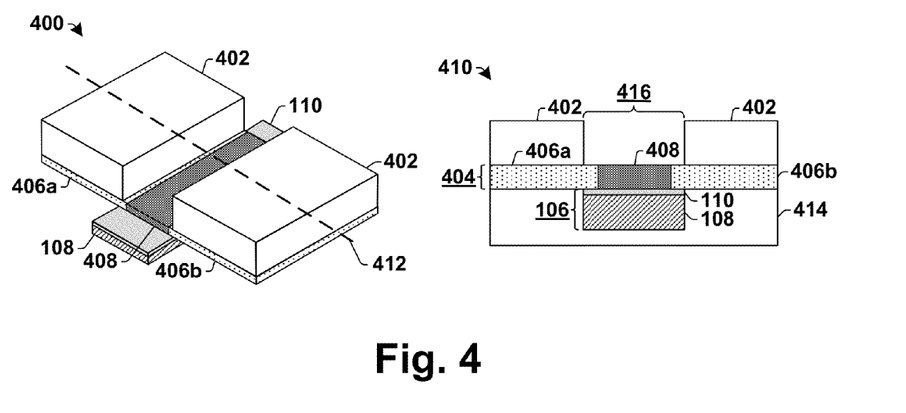
FIGS. 4-6 illustrate some embodiments of a substrate on which a method of forming a disclosed nanowire structure, corresponding to the method of FIG. 3, is performed.
Figure 5:
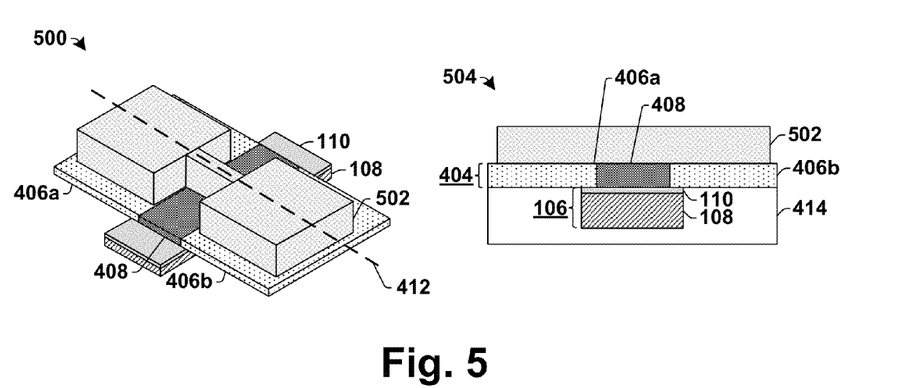
Figure 6:
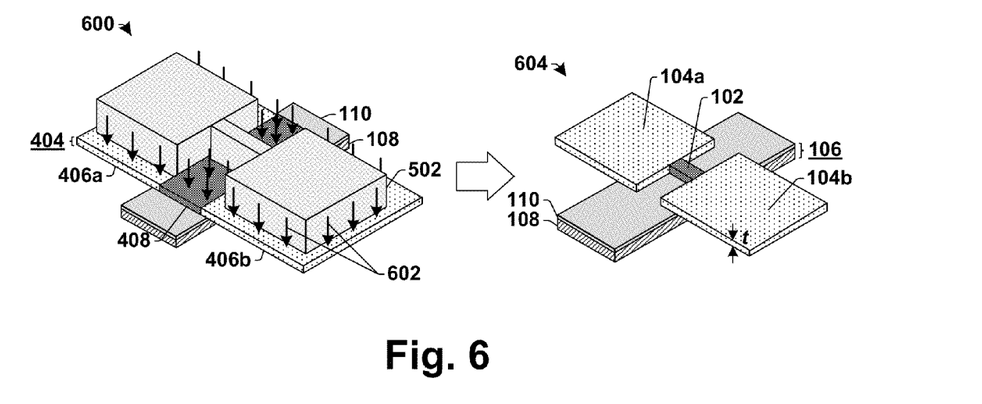

FIGS. 4-6 illustrate some embodiments of a substrate on which a method of forming a disclosed nanowire structure, corresponding to method 300, is performed. Although FIGS. 4-6 are described in relation to method 300, it will be appreciated that the structures disclosed in FIGS. 4-6 are not limited to such a method, but instead may stand alone as a structure.

FIG. 4 illustrates some embodiments of a substrate corresponding to act 302. FIG. 4 illustrates a three-dimensional view 400 and a corresponding cross-sectional view 410 extending along a cross-sectional line 412.

The substrate comprises a device layer 404 disposed over a gate structure 106. The device layer 404 comprises a source region 406a and a drain region 406b separated by a device material 408 (e.g., a semiconductor material). The gate structure 106 comprises a gate material layer 108 and a gate dielectric layer 110 disposed between the gate material layer 108 and a device layer 404. In some embodiments, the gate structure 106 may be formed within a dielectric layer 414.

In some embodiments, a dielectric material 402 may overlay the device layer 404, so that the device layer 404 disposed between the gate structure 106 and dielectric material 402. The dielectric material 402 may comprise an opening 416 that allows for a medium to contact the device layer 404. In some embodiments, the dielectric material 402 may comprise an oxide or a passivation layer (e.g., a nitride, polymer). The overlying dielectric material 402 may be removed to expose the source and drain regions, 406a and 406b, prior to act 304.

FIG. 5 illustrates some embodiments of a substrate corresponding to act 304. FIG. 5 illustrates a three-dimensional view 500 and a corresponding cross-sectional view 504 extending along a cross-sectional line 412.

As shown in FIG. 4, a masking layer 502 is selectively formed over the device layer 404 after removing the dielectric 402 to define a nanowire structure within the device material 408. In some embodiments, the masking layer 502 may be selectively formed over the device layer 404 using a photolithography process. For example, a photoresist material may be deposited over the device layer 404 and then selectively exposed and developed to form the masking layer 502.

FIG. 6 illustrates some embodiments of a substrate corresponding to act 306. FIG. 6 illustrates a three-dimensional view 600 showing the substrate during etching and a three-dimensional view 604 showing the substrate after etching is completed.

As shown in three-dimensional view 600, the device layer 404 is selectively etched, by an etchant 602, according to the masking layer 502. The position of the gate structure 106 below the device layer 404 allows for the device layer 404 to be exposed to the etchant 602 from a side of the device layer 404 that opposes the gate structure 106. The etchant 602 removes a portion of the device material 408 to form a wire-like nanowire structure 102 extending between the source region 104a and the drain region 104b, as shown in three-dimensional view 604. In some embodiments, the etchant 602 may also remove a portion of the source region 104a and the drain region 104b. In some embodiments, the etchant 602 may comprise one or more different etching steps (e.g., respectively configured to selectively remove different materials). The different etching steps can include wet etching and/or dry etching steps, wherein different etching steps comprise different etchants.

By selectively etching the device layer 404 to form a nanowire structure 102 that extends between the source region 104a and the drain region 104b, the nanowire structure 102 is automatically connected to the source region 104a and to the drain region 104b, thereby ensuring good contact without having to manually secure the nanowire structure 102 to the source region 104a and to the drain region 104b.

In various embodiments, the etchant 602 may comprise a wet etchant or a dry etchant. For example, the etchant 602 may comprise a dry etchant having a chemistry comprising $CF_4$. In some embodiments, the etching process may be configured to reduce a final thickness t of the device layer 404, so that the height of the nanowire structure 102 is less than the original thickness of the device layer 404.

Figure 7:
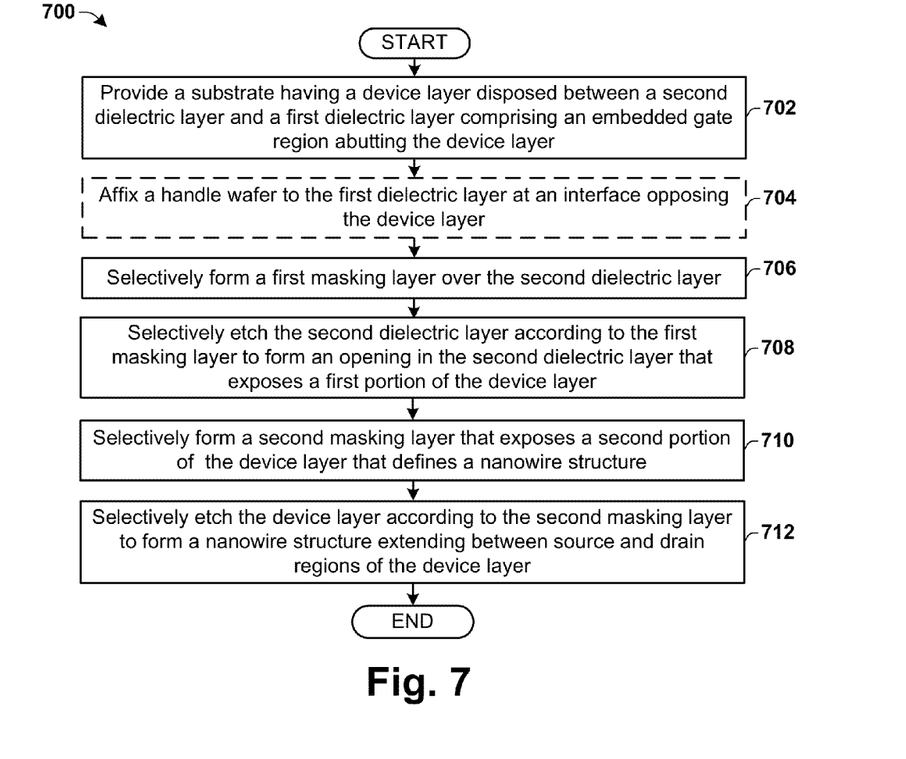
FIG. 7 illustrates some embodiments of an additional top-down method of forming a disclosed nanowire structure on a nanowire transistor device

FIG. 7 illustrates some embodiments of an additional top-down method 700 of forming a disclosed nanowire structure on a nanowire transistor device.

It will be appreciated that while the disclosed methods (e.g., methods 300 and 700) are illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 702, a substrate having a device layer disposed between a first dielectric layer and a second dielectric layer is provided. The first dielectric layer comprises an embedded gate region abutting the device layer, which comprises a source region and a drain region separated by a device material (e.g., a semiconductor material). In some embodiments, one or more metallization layers may be formed within the first dielectric layer to provide an electrical connection between the source region, the drain region, and/or the embedded gate region and an input/output terminal of an integrated chip (e.g., to a bonding pad).

At 704, a handle wafer may be affixed to the first dielectric layer at an interface opposing the device layer.

At 706, a first masking layer is formed over the second dielectric layer.

At 708, the second dielectric layer is selectively etched according to the first masking layer to form an opening in the second dielectric layer that exposes a first portion of the device layer.

At 710, a second masking layer is formed. The second masking layer exposes a second portion of the device layer that defines a nanowire structure.

At 712, the device layer is selectively etched according to the second masking layer to form a nanowire structure extending between source and drain regions of the device layer.

FIGS. 8-12 illustrate some embodiments of a substrate on which a method of forming a disclosed nanowire structure, according to method 700, is performed. Although FIGS. 8-12 are described in relation to method 700, it will be appreciated that the structures disclosed in FIGS. 8-12 are not limited to such a method, but instead may stand alone as a structure.

Figure 8:
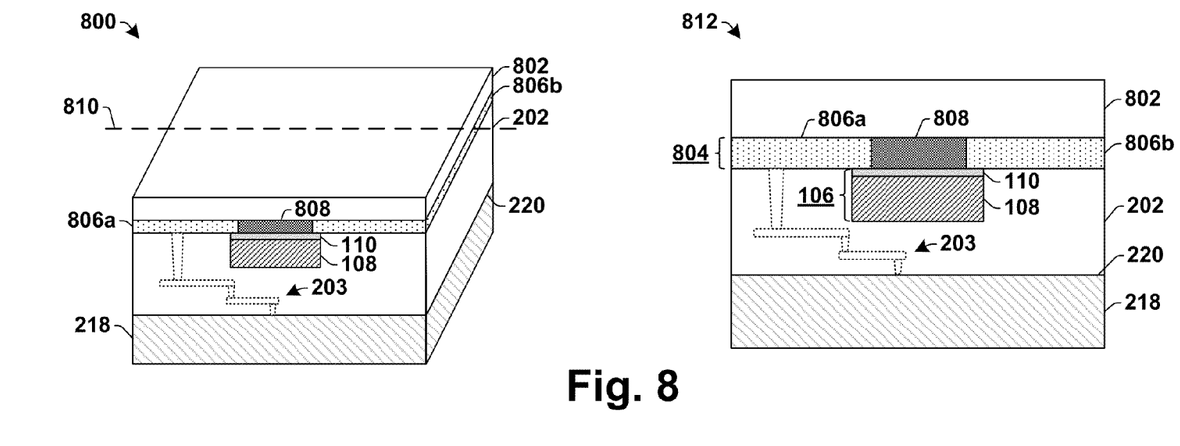
FIGS. 8-12 illustrate some embodiments of a substrate on which a method of forming a disclosed nanowire structure, corresponding to the method of FIG. 7, is performed.

FIG. 8 illustrates some embodiments of a substrate corresponding to acts 702-704. FIG. 8 illustrates a three-dimensional view 800 and a corresponding cross-sectional view 812 extending along a cross-sectional line 810.

The substrate comprises a device layer 804 disposed between a first dielectric layer 202 and a second dielectric layer 802. The device layer 804 comprises a semiconductor material (e.g., silicon) having a source region 806a and a drain region 806b. The source and drain regions, 806a and 806b, are separated by a device material 808 (e.g., a semiconductor material). In some embodiments, the source and drain regions, 806a and 806b, comprise a semiconductor material having a higher dopant concentration than the device material 808.

The first and second dielectric layers, 202 and 802, may comprise an oxide (e.g., $SiO_2$) or other dielectric material (e.g., SiCO). The first dielectric layer 202 comprises an embedded gate structure 106 having a gate material layer 108 and a gate dielectric layer 110. The gate material layer 108 is separated from the device layer 804 by the gate dielectric layer 110. In some embodiments, the gate material layer 108 may comprise a polysilicon or a metal gate material (e.g., aluminum). The gate dielectric layer 110 may comprise an oxide (e.g., $SiO_2$). The second dielectric layer 802 is disposed along a side of the device layer 804 opposing the gate structure 106. In some embodiments, one or more metal interconnect layers 203 (e.g., metal wires and/or metal vias) are disposed within the first dielectric layer 202.

In some embodiments, the substrate is coupled to a handle wafer 218 at an interface 220. In some embodiments, the substrate may be coupled to the handle wafer 218 by bonding the handle wafer to the first dielectric layer 202 (e.g., using fusion bonding). In other embodiments, substrate may be coupled to the handle wafer 218 by forming the substrate upon the handle wafer 218. For example, the first dielectric layer 202 may be grown onto the handle wafer 218 during fabrication. The handle wafer 218 is configured to provide rigid support to the substrate. In some embodiments, the handle wafer 218 may comprise a silicon wafer, for example.

Figure 9:
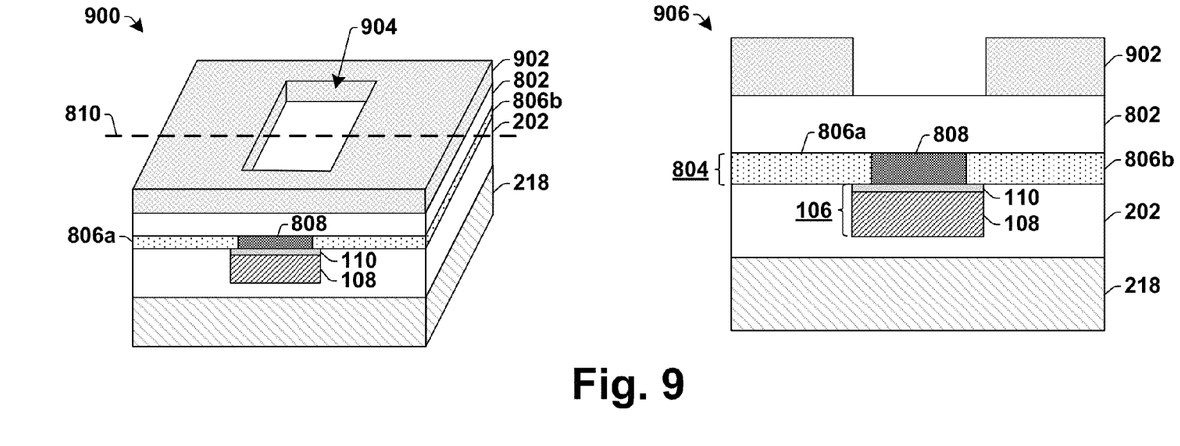

FIG. 9 illustrates some embodiments of a substrate corresponding to act 706. FIG. 9 illustrates a three-dimensional view 900 and a corresponding cross-sectional view 906 extending along cross-sectional line 810.

As shown, a first masking layer 902 is selectively formed over the second dielectric layer 802. The first masking layer 902 is formed to have an opening 904 that exposes a first portion of the second dielectric layer 802 that overlies the device material 808 of the device layer 804. In some embodiments, the first portion of the second dielectric layer 802 may also overlie a portion of the source and drain regions, 806a and 806b. In some embodiments, the first masking layer 902 may comprise a photoresist layer patterned by a photoresist process, for example.

Figure 10:
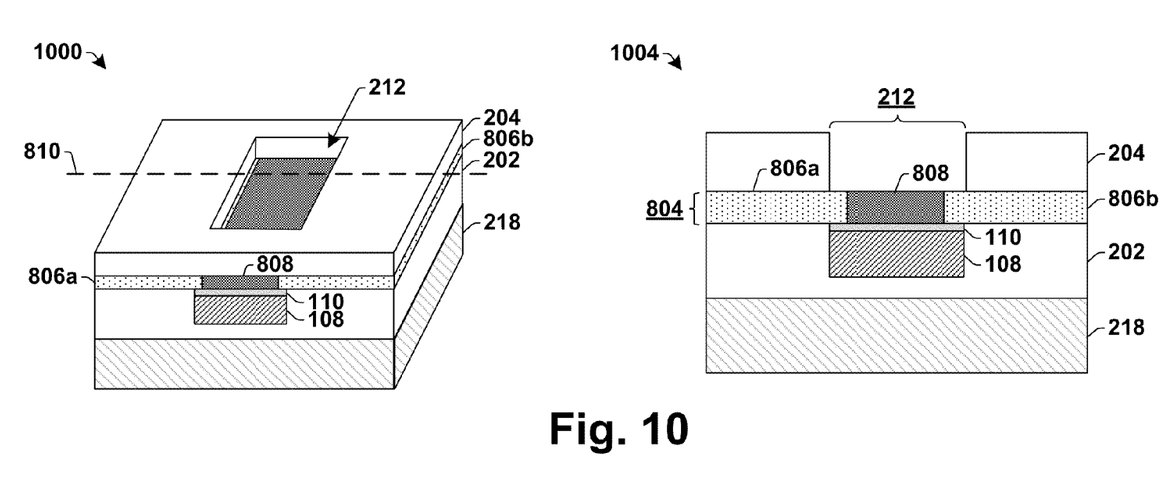

FIG. 10 illustrates some embodiments of a substrate corresponding to act 708. FIG. 10 illustrates a three-dimensional view 1000 and a corresponding cross-sectional view 1004 extending along cross-sectional line 810.

As shown, selective etching of the substrate according to the first masking layer 902 results in a second dielectric layer 204 having an opening 212. The opening 212 exposes a first portion of the device layer 804 comprising the device material 808. In some embodiments, the opening 212 may also expose a portion of the source and/or drain regions, 806a and/or 806b.

Figure 11:
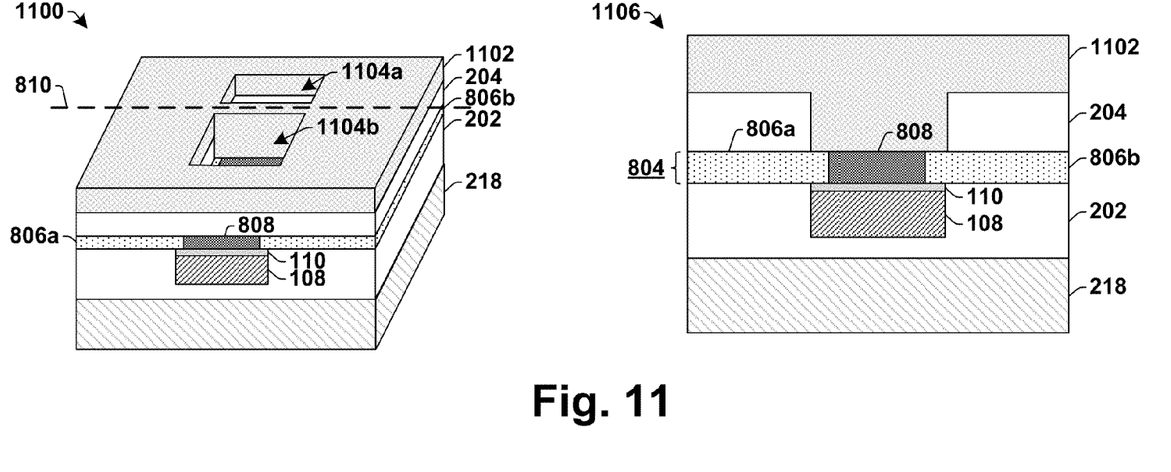

FIG. 11 illustrates some embodiments of a substrate corresponding to act 710. FIG. 11 illustrates a three-dimensional view 1100 and a corresponding cross-sectional view 1106 extending along cross-sectional line 810.

As shown, a second masking layer 1102 is selectively formed over the second dielectric layer 204. The second masking layer 1102 extends over the exposed first portion of the device layer 804 as a bridge to form a first opening 1104a and a second opening 1104b in the second masking layer 1102. The first and second openings, 1104a and 1104b, which collectively expose a second portion of the device layer 804 that defines a nanowire structure. For example, the first and second openings, 1104a and 1104b, expose a portion of the device material 808 extending between the source and drain regions, 806a and/or 806b, while covering (i.e., masking) the device material 808 at a position corresponding to a position of a nanowire structure to be formed. In some embodiments, the second masking layer 1102 is overlaid over a portion of the source and drain regions, 806a and/or 806b, abutting the device material 808.

Figure 12:
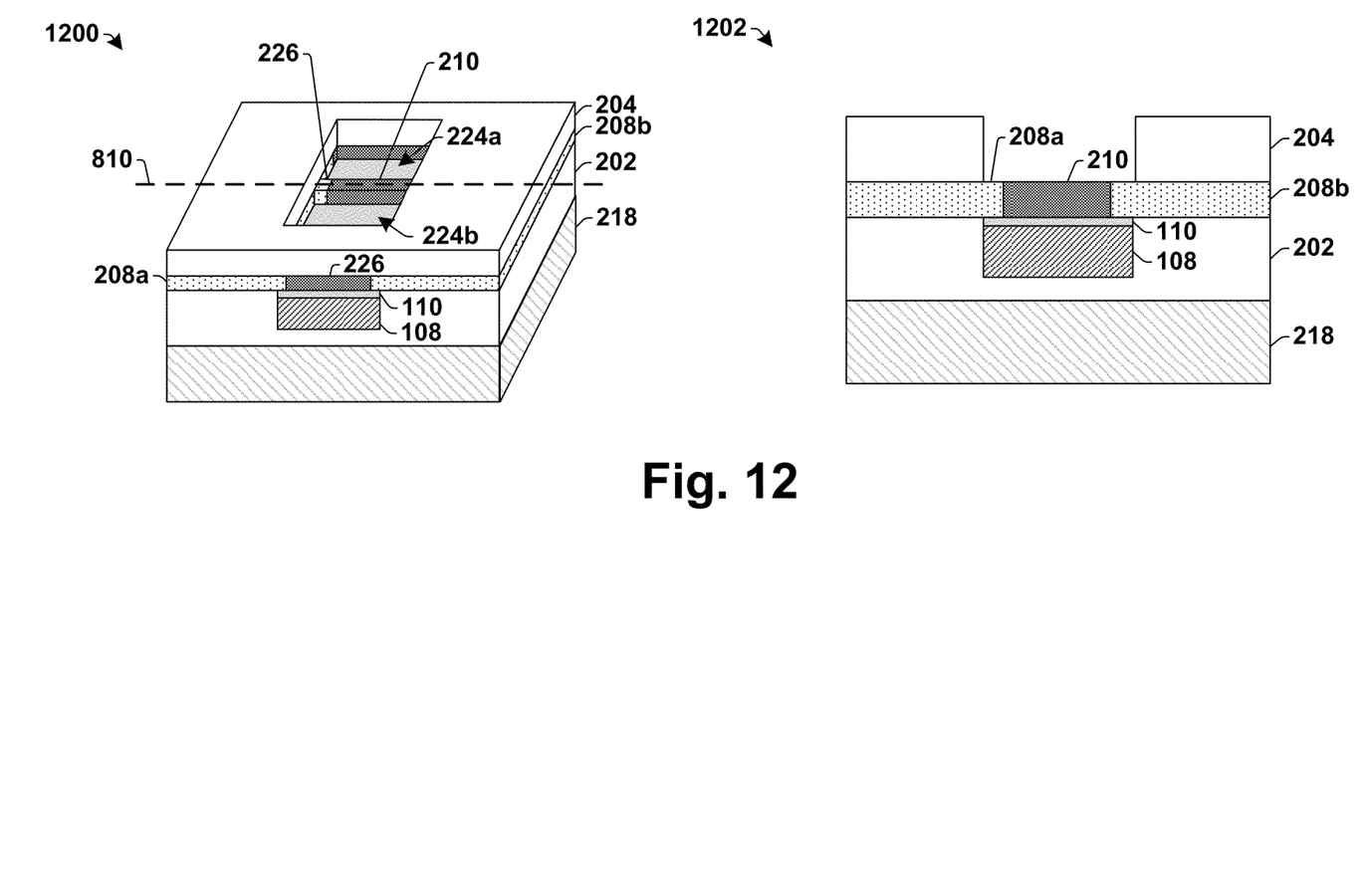

FIG. 12 illustrates some embodiments of a substrate corresponding to act 712. FIG. 12 illustrates a three-dimensional view 1200 and a corresponding cross-sectional view 1202 extending along cross-sectional line 810.

As shown, the substrate is selectively etched according to the second masking layer 1102 to form a pair of openings, 224a and 224b, in the device layer 804. The pair of openings, 224a and 224b, abut opposite sides of the nanowire structure 210, which extends between the source and drain regions, 208a and 208b. The pair of openings, 224a and 224b, expose a portion of the underlying gate dielectric layer 110, such that the device layer 804 is removed within the pair of openings, 224a and 224b. In some embodiments, the substrate may be selectively etched using one or more different etching steps (e.g., respectively configured to selectively remove different materials). The different etching steps can include wet etching and/or dry etching steps, wherein different etching steps comprise different etchants.

In some embodiments, wherein the pair of openings, 224a and 224b, expose a portion of the source and/or drain regions, 208a and/or 208b, the selective etching of act 712 results in source and drain regions, 208a and/or 208b, having a bulge 226 (i.e., the source and drain regions are not square, but instead comprise a square shape having a bulge). The bulge 226 protrudes from the sidewalls of the source and drain regions, 208a and/or 208b, and connects the source and drain regions, 208a and/or 208b, underlying the second dielectric layer 204 to the nanowire structure 210. In other embodiments, non-bulge shaped structures of the source and drain regions, 208a and/or 208b, may be exposed.

It will be appreciated that while reference is made throughout this document to exemplary structures in discussing aspects of methodologies described herein, those methodologies are not to be limited by the corresponding structures presented. Rather, the methodologies and structures are to be considered independent of one another and able to stand alone and be practiced without regard to any of the particular aspects depicted in the Figs.

Also, equivalent alterations and/or modifications may occur to one of ordinary skill in the art based upon a reading and/or understanding of the specification and annexed drawings. The disclosure herein includes all such modifications and alterations and is generally not intended to be limited thereby. For example, although the figures provided herein are illustrated and described to have a particular doping type, it will be appreciated that alternative doping types may be utilized as will be appreciated by one of ordinary skill in the art.

In addition, while a particular feature or aspect may have been disclosed with respect to one of several implementations, such feature or aspect may be combined with one or more other features and/or aspects of other implementations as may be desired. Furthermore, to the extent that the terms "includes", "having", "has", "with", and/or variants thereof are used herein, such terms are intended to be inclusive in meaning—like "comprising." Also, "exemplary" is merely meant to mean an example, rather than the best. It is also to be appreciated that features, layers and/or elements depicted herein are illustrated with particular dimensions and/or orientations relative to one another for purposes of simplicity and ease of understanding, and that the actual dimensions and/or orientations may differ from that illustrated herein.

Therefore, the present disclosure relates to a top-down method of forming a nanowire structure extending between source and drain regions of a nanowire transistor device, and an associated apparatus.

In some embodiments, the present disclosure relates to a method of forming a nanowire transistor device. The method comprises providing a substrate having a device layer disposed over a first dielectric layer comprising an embedded gate structure abutting the device layer, wherein the device layer comprises a source region and a drain region separated by a device material. The method further comprises selectively forming one or more masking layers over the device layer at one or more positions that define a nanowire structure. The method further comprises selectively etching the device layer according to the one or more masking layers to form the nanowire structure at a position between the source region and the drain region.

In other embodiments, the present disclosure relates to a method of forming a nanowire transistor device. The method comprises providing a substrate having a device layer disposed between a first dielectric layer and a second dielectric layer, wherein the first dielectric layer comprises an embedded gate structure abutting the device layer. The method further comprises forming a first masking layer on the second dielectric layer. The method further comprises selectively etching the second dielectric layer according to the first masking layer to form an opening in the second dielectric layer that exposes a first portion of the device layer. The method further comprises forming a second masking layer that exposes a second portion of the device layer that defines a nanowire structure. The method further comprises selectively etching the device layer according to the second masking layer to form the nanowire structure, which extends between a source region and a drain region within the device layer.

In other embodiments, the present disclosure relates to a nanowire transistor device. The transistor device comprises a nanowire structure disposed within a device layer. The transistor device comprises an upper dielectric layer disposed over the nanowire structure and having an opening that exposes the nanowire structure to an ambient environment. The nanowire structure comprises a height and a width having dimensions that are comparable to a biomarker that is to be detected by the nanowire device.

What is claimed is:

1. A method of forming a nanowire transistor device, comprising:
    providing a substrate having a device layer disposed over a first dielectric layer that surrounds an embedded gate structure having a gate electrode and a gate dielectric layer with sidewalls abutting the first dielectric layer, wherein the device layer comprises a source region and a drain region separated by a device material;
    selectively forming one or more masking layers over the device layer at one or more positions that define a nanowire structure; and
    selectively etching the device layer according to the one or more masking layers to form the nanowire structure at a position between the source region and the drain region.

2. The method of claim 1, further comprising:
    forming one or more metal interconnect layers within the first dielectric layer.

3. The method of claim 1, wherein the source region and the drain region respectively comprise a bulge that protrudes from sidewalls of the source region and the drain region at a position that connects the source region and the drain region to the nanowire structure.

4. The method of claim 1, further comprising:
    forming a second dielectric layer over the device layer along a side of the device layer that opposes the embedded gate structure.

5. The method of claim 1, wherein forming one or more masking layers over the device layer, comprises:
    etching the second dielectric layer according to a first masking layer to form an opening in the second dielectric layer that exposes the device material and the source and drain regions; and
    etching sections of the device material and the source and drain regions that are exposed by the opening according to a second masking layer that masks a second portion of the device material comprising the nanowire structure.

6. The method of claim 5, wherein the first masking layer and the second masking layer are selectively patterned using a lithographic process.

7. The method of claim 1, further comprising:
    affixing a handle wafer to the first dielectric layer at an interface along a side of the first dielectric layer that opposes the device layer, wherein the handle wafer is configured to provide rigid support to the substrate.

8. The method of claim 1, wherein the source region and the drain region comprise a semiconductor material having a higher dopant concentration than the nanowire structure located therebetween.

9. The method of claim 1, wherein selectively etching the device layer comprises exposing the device layer to an etchant from a side of the device layer that opposes the gate structure.

10. A method of forming a nanowire transistor device, comprising:
provoding a substrate having a device layer disposed between a first dielectric layer and a second dielectric layer, wherein the first dielectric layer comprises an embedded gate structure abutting the device layer;
forming a first masking layer on the second dielectric layer;
selectively etching the second dielectric layer according to the first masking layer to form an opening in the second dielectric layer that exposes a first portion of the device layer;
forming a second masking layer onto the second dielectric layer, wherein the second masking layer exposes a second portion of the device layer that defines a nanowire structure; and
selectively etching sections of the device layer exposed by the opening according to the second masking layer to form the nanowire structure, which extends between a source region and a drain region within the device layer.

11. The method of claim 10, wherein the nanowire structure comprises a height and a width having dimensions that are comparable to a biomarker or byproducts from biological activities that is/are to be detected by the nanowire transistor device.

12. The method of claim 10, wherein the source region and the drain region respectively comprise a bulge that protrudes from sidewalls of the source region and the drain region at a position that connects the source region and the drain region to the nanowire structure.

13. The method of claim 10, further comprising:
affixing a handle wafer to the first dielectric layer at an interface along a side of the first dielectric layer that opposes the device layer, wherein the handle wafer is configured to provide rigid support to the substrate.

14. The method of claim 10, wherein the source region and the drain region comprise a semiconductor material having a higher dopant concentration than the nanowire structure located therebetween.

15. The method of claim 10, wherein selectively etching the device layer comprises exposing the device layer to an etchant from a side of the device layer that opposes the gate structure.

16. A nanowire transistor device, comprising:
a lower dielectric layer that surrounds an embedded gate structure having a gate electrode and a gate dielectric layer with sidewalls abutting the lower dielectric layer;
a device layer abutting the gate dielectric layer;
a source region disposed within the device layer at a first position over the lower dielectric layer;
a drain region disposed within the device layer at a second position over the lower dielectric layer;
a nanowire structure disposed within the device layer at third a position over the lower dielectric layer and between the source region and the drain region; and
an upper dielectric layer disposed over the nanowire structure and having an opening that exposes the nanowire structure to an ambient environment.

17. The nanowire transistor device of claim 16, wherein the source region and the drain region respectively comprise a bulge that protrudes from sidewalls of the source region and the drain region at a position that connects the source region and the drain region to the nanowire structure.

18. The nanowire transistor device of claim 16, further comprising one or more metal interconnect layers disposed within the lower dielectric layer.

19. The nanowire transistor device of claim 16,
wherein the nanowire structure extends between the source region and the drain region in a first direction, and
wherein the source region and the drain region extend past the gate structure in the first direction.

20. The nanowire transistor of claim 16, wherein the gate dielectric layer and the gate electrode have substantially aligned sidewalls.

* * * * *